(12) United States Patent
Kharas et al.

(10) Patent No.: US 8,399,715 B2
(45) Date of Patent: *Mar. 19, 2013

(54) COBALT-MOLYBDENUM SULFIDE CATALYST MATERIALS AND METHODS FOR ETHANOL PRODUCTION FROM SYNGAS

(75) Inventors: Karl Kharas, Louisville, CO (US); Jason P. Durand, Thornton, CO (US)

(73) Assignee: Albemarle Corporation, Baton Rouge, LA (US)

( * ) Notice: Subject to any disclaimer, the term of this patent is extended or adjusted under 35 U.S.C. 154(b) by 9 days.

This patent is subject to a terminal disclaimer.

(21) Appl. No.: 13/039,007

(22) Filed: Mar. 2, 2011

(65) Prior Publication Data

US 2011/0160317 A1  Jun. 30, 2011

Related U.S. Application Data

(62) Division of application No. 12/204,543, filed on Sep. 4, 2008, now Pat. No. 7,923,405.

(51) Int. Cl.
| | |
|---|---|
| C07C 29/00 | (2006.01) |
| C07C 31/00 | (2006.01) |
| C07C 31/02 | (2006.01) |
| C07C 33/00 | (2006.01) |
| C07C 27/00 | (2006.01) |
| C07C 27/06 | (2006.01) |
| B01J 27/02 | (2006.01) |
| B01J 27/051 | (2006.01) |
| B01J 27/049 | (2006.01) |
| B01J 27/043 | (2006.01) |

(52) U.S. Cl. ........ 568/840; 502/216; 502/220; 502/221; 502/222; 518/714; 518/715

(58) Field of Classification Search ................ 568/840; 502/216, 220–222; 518/714, 715
See application file for complete search history.

(56) References Cited

U.S. PATENT DOCUMENTS

| | | | | | |
|---|---|---|---|---|---|
| 2,629,729 | A | * | 2/1953 | Layng | 518/719 |
| 2,767,202 | A | * | 10/1956 | Rottig | 518/713 |
| 4,752,622 | A | * | 6/1988 | Stevens | 518/714 |
| 4,752,623 | A | * | 6/1988 | Stevens et al. | 518/714 |
| 7,923,405 | B2 | * | 4/2011 | Kharas et al. | 502/216 |
| 2010/0076228 | A1 | * | 3/2010 | Alsum et al. | 568/840 |
| 2010/0152498 | A1 | * | 6/2010 | Kharas et al. | 568/840 |
| 2010/0210741 | A1 | * | 8/2010 | Kharas | 518/714 |
| 2010/0280287 | A1 | * | 11/2010 | Kharas et al. | 568/840 |

* cited by examiner

Primary Examiner — Patricia L Hailey
(74) Attorney, Agent, or Firm — Jeremy J. Kliebert; Marcy M. Hoefling; James A. Jubinsky (57) ABSTRACT

The present invention provides methods and compositions for the chemical conversion of syngas to alcohols. The invention includes catalyst compositions, methods of making the catalyst compositions, and methods of using the catalyst compositions. Certain embodiments teach compositions for catalyzing the conversion of syngas into products comprising at least one $C_1$-$C_4$ alcohol, such as ethanol. These compositions generally include cobalt, molybdenum, and sulfur. Preferred catalyst compositions for converting syngas into alcohols include cobalt associated with sulfide in certain preferred stoichiometries as described and taught herein.

20 Claims, 4 Drawing Sheets

COBALT-MOLYBDENUM SULFIDE CATALYST MATERIALS AND METHODS FOR ETHANOL PRODUCTION FROM SYNGAS

PRIORITY DATA

This divisional patent application claims priority to U.S. patent application Ser. No. 12/204,543 filed Sep. 4, 2008, which in turn claims priority to U.S. Provisional Patent Application No. 60/970,644 filed Sep. 7, 2007, each of which are hereby incorporated by reference herein for all purposes.

FIELD OF THE INVENTION

The present invention generally relates to the field of catalysts for the chemical conversion of synthesis gas to alcohols. The invention relates to catalyst compositions, methods of using the catalyst compositions, methods of maintaining catalytic activity, and methods of making catalysts.

BACKGROUND OF THE INVENTION

Synthesis gas (hereinafter referred to as syngas) is a mixture of hydrogen ($H_2$) and carbon monoxide (CO). Syngas can be produced, in principle, from virtually any feedstock material containing carbon. Carbonaceous materials commonly include fossil resources such as natural gas, petroleum, coal, and lignite. Renewable resources such as lignocellulosic biomass and various carbon-rich waste materials can also be used to produce syngas. It is preferable to utilize a renewable resource to produce syngas because of the rising economic, environmental, and social costs associated with fossil resources.

There exist a variety of conversion technologies to turn these various feedstocks into syngas. Conversion approaches can utilize a combination of one or more steps comprising gasification, pyrolysis, steam reforming, and/or partial oxidation of a carbon-containing feedstock.

Syngas is a platform intermediate in the chemical and biorefining industries and has a vast number of uses. Syngas can be converted into alkanes, olefins, oxygenates, and alcohols. These chemicals can be blended into, or used directly as, diesel fuel, gasoline, and other liquid fuels. Syngas can also be directly combusted to produce heat and power.

Since the 1920s it has been known that mixtures of methanol and other alcohols can be obtained by reacting syngas over certain catalysts (Forzatti et al., *Cat. Rev.—Sci. and Eng.* 33(1-2), 109-168, 1991). Fischer and Tropsch observed around the same time that hydrocarbon-synthesis catalysts produced linear alcohols as byproducts (Fischer and Tropsch, *Brennst.—Chem.* 7:97, 1926).

Technology developers for these catalysts have included Dow Chemical/Union Carbide and Institut Francais du Petrole. Dow Chemical and Union Carbide jointly developed a sulfided mixed-alcohol catalyst based on molybdenum, $MoS_2$ (Phillips et al., National Renewable Energy Laboratory TP-510-41168, April 2007).

U.S. Pat. No. 4,752,623 (Stevens and Conway), originally assigned to Dow Chemical, discloses a catalyst for producing mixed alcohols from syngas, wherein the catalyst contains either molybdenum or tungsten, in addition to either cobalt or nickel, both components being in sulfided form. Stevens and Conway emphasize that it is not necessary for their invention that any particular stoichiometric metal sulfide be present. Sulfided cobalt is often assigned to CoS in the literature. Further, Stevens and Conway state that no advantage is realized by the presence of sulfur in the feed.

Another development at Dow Chemical, related to a similar catalyst preparation by Dianis, involves addition of aqueous cobalt acetate to ammonium molybdate in 30% acetic acid solution. Both the Dianis as well as the Stevens/Conway approaches employ decomposition under $N_2$ at 500° C. Dianis mentions the presence of a peak in the powder X-ray diffraction pattern that is tentatively assigned to $CoS_2$, but there is no discussion as to whether the presence of $CoS_2$ is favorable or unfavorable (Dianis, *Applied Catalysis* 39, 99-121, 1987).

More recently, Iranmahboob and Hill (*Catalysis Letters* 78, 49-55, 2002) discussed similar catalysts for synthesis of higher alcohols. Iranmahboob and Hill found $Co_3S_4$ present in their better catalysts and $Co_9S_8$ present in their inferior catalysts. They hypothesized that, in their system, $H_2S$ evolution results in transformation of more-active $Co_3S_4$ into less-active $Co_9S_8$.

The existing art provides little, if any, information concerning chemical or physical characteristics that tend to correlate with the performance of cobalt-molybdenum-sulfide alcohol-synthesis catalysts, including Co—Mo—S, and similar catalyst systems comprising Ni and/or W. Particularly absent is information relating to preferred amounts of sulfur, on a stoichiometric basis, relative to other major components present. Also particularly absent is information relating to the preferred nature of the physical and/or chemical bonds or associations among at least Co, Mo, and S.

In light of these shortcomings in the art, what is needed is a novel and non-obvious discovery that reveals and distinctly teaches improved catalyst compositions in a manner that enables a person skilled in the art to make and use the catalyst compositions. Especially needed are preferred methods of making these catalyst compositions, and preferred methods of using these catalyst compositions, to convert syngas into alcohols. An especially preferred alcohol is ethanol, which can replace gasoline and other liquid fuels, at least in part, today.

SUMMARY OF THE INVENTION

In a first aspect of the present invention, compositions are provided for catalyzing the conversion of syngas into products comprising at least one $C_1$-$C_4$ alcohol, the composition comprising cobalt, molybdenum, and sulfur, wherein at least some of the cobalt and some of the sulfur are present as a cobalt-sulfur association, and wherein the molar ratio of sulfur to cobalt (S:Co) in the association is at least 1.2, the molar ratio S:Co calculated after assigning some of the sulfur to molybdenum by assuming all molybdenum is present in the composition as $MoS_2$.

In some embodiments, the molar ratio S:Co is at least 1.5, at least 2.0, or between about 2.0 and about 4.0. The molar ratio S:Co can be calculated after assigning some of the sulfur to molybdenum by assuming all molybdenum is present in the composition as $MoS_2$, and after subtracting any elemental sulfur present. Optionally, S:Co can further be calculated after subtracting any sulfur that is soluble in 3 N HCl.

In some embodiments, the cobalt is present in an amount between about 3-21 wt %, such as about 10-16 wt %, of the composition. In some embodiments, the molybdenum is present in an amount between about 33-56 wt % of the composition. The molar ratio of the molybdenum to the cobalt can be from about 1.5 to about 8, such as about 2.

The sulfur can be present in a total amount of at least 40 wt % of the composition, such as about 42-44 wt %. The sulfur can include elemental sulfur in an amount of at least 100 ppm, such as about 150-5000 ppm or about 300-1000 ppm of the composition. In some embodiments, at least 0.02% or 0.05% of the sulfur is capable of leaching into chloroform at 55° C. In certain embodiments, between about 0.02% and about 0.1% of the sulfur is capable of leaching into chloroform at 55° C.

In some embodiments, less than about 8%, preferably less than 3%, of the cobalt is capable of leaching into a 3N HCl solution at 90° C. In certain embodiments, substantially no cobalt is capable of leaching into a 3N HCl solution at 90° C.

In some embodiments, less than about 0.5%, preferably less than 0.3%, of the molybdenum is capable of leaching into a 3N HCl solution at 90° C. In certain embodiments, substantially no molybdenum is capable of leaching into a 3N HCl solution at 90° C.

When, for example, alcohols are desired products from syngas using these catalyst compositions, the compositions of the invention can further comprise one or more base promoters selected from the group consisting of potassium, rubidium, cesium, barium, strontium, scandium, yttrium, lanthanum, cerium, and any combinations thereof.

One exemplary catalyst composition for catalyzing the conversion of syngas into at least some ethanol, comprises 13-15 wt % total cobalt, 40-45 wt % total molybdenum, at least 40 wt % total sulfur, and an effective amount of a base promoter, wherein (i) the total sulfur includes between 250-750 ppm elemental sulfur; (ii) at least some of the total cobalt and some of the total sulfur are present as a cobalt-sulfur association having a molar ratio of sulfur to cobalt (S:Co) of at least 2.0, the molar ratio S:Co calculated assuming all molybdenum is present as $MoS_2$, and after subtracting sulfur that is capable of leaching into chloroform or 3 N HCl at 25° C.; (iii) less than about 3% of the total cobalt is capable of leaching into a 3N HCl solution at 90° C.; and (iv) less than about 0.5% of the total molybdenum is capable of leaching into a 3N HCl solution at 90° C.

In a second aspect of the invention, compositions are provided for catalyzing the conversion of syngas into products comprising at least one $C_1$-$C_4$ alcohol, the composition comprising sulfur, a first element or plurality of elements E1 and a second element or plurality of elements E2, wherein: E1 is cobalt and/or nickel; E2 is molybdenum and/or tungsten; at least some of E1 and some of the sulfur are present as an E1-sulfur association; and the molar ratio of sulfur to E1 (S:E1) in the association is at least 1.2, the molar ratio S:E1 calculated after assigning some of the sulfur to E2 by assuming all E2 is present in the composition as $E2S_2$.

The molar ratio S:E1 can be at least 1.5, such as about 2.0-4.0. In some embodiments, the molar ratio S:E1 calculated after assigning some of the sulfur to E2 by assuming all E2 is present in the composition as $E2S_2$, and after subtracting any sulfur that is soluble in chloroform and/or 3 N HCl.

In some embodiments of this second aspect, the sulfur can be present in a total amount of at least 30 wt % of the composition. The sulfur can include elemental sulfur in an amount of at least 100 ppm of the composition. In certain embodiments, at least 0.02% of the sulfur is capable of leaching into chloroform at 55° C.

The molar ratio of E2 to E1 can be selected from about 1 to about 20. In some embodiments, the molar ratio of E2 to E1 is from about 1.5-8. The compositions of this second aspect can also be characterized by leachability; in some embodiments less than about 8% of the E1 is capable of leaching into a 3N HCl solution at 90° C., and less than about 0.5% of the E2 is capable of leaching into a 3N HCl solution at 90° C.

The compositions of this second aspect can further comprise one or more base promoters selected from the group consisting of potassium, rubidium, cesium, barium, strontium, scandium, yttrium, lanthanum, cerium, and any combinations thereof.

A third aspect of this invention provides methods of producing at least one $C_1$-$C_4$ alcohol (such as ethanol) from syngas, the method comprising:
(a) providing a reactor;
(b) providing a first catalyst composition comprising cobalt, molybdenum, sulfur, and a base promoter, wherein at least some of the cobalt and some of the sulfur are present as a cobalt-sulfur association having a first molar ratio of sulfur to cobalt, calculated by assuming all molybdenum is present as $MoS_2$;
(c) activating the first catalyst composition by contact with a stream comprising syngas, under suitable conditions for catalyst activation, thereby producing a second catalyst composition having a second molar ratio of sulfur to cobalt; and
(d) flowing syngas into the reactor at conditions effective to produce at least one $C_1$-$C_4$ alcohol,
wherein the second molar ratio of sulfur to cobalt is lower than the first molar ratio of sulfur to cobalt.

In some of these methods, the first molar ratio of sulfur to cobalt is at least 1.2. In some embodiments, the second molar ratio of sulfur to cobalt is 1.5 or less, such as 0.5 or less. In certain embodiments, the first molar ratio of sulfur to cobalt is at least 2 and the second molar ratio of sulfur to cobalt is 1.4 or less.

The activating step (c) can be performed within the reactor provided in step (a).

In some embodiments of this third aspect, a first amount of total cobalt contained in the first catalyst composition is capable of leaching into a 3N HCl solution, a second amount of total cobalt contained in the second catalyst composition is capable of leaching into a 3N HCl solution, and the second amount of cobalt is greater than the first amount of cobalt.

The first amount of total cobalt capable of leaching into a 3N HCl solution can be less than about 10%. The second amount of total cobalt capable of leaching into a 3N HCl solution can be greater than about 40%.

In a fourth aspect of the invention, activated catalyst compositions are produced by the process of:
(a) providing a precursor catalyst composition comprising cobalt, molybdenum, sulfur, and a base promoter, wherein at least some of the cobalt and some of the sulfur are present as a cobalt-sulfur association having a first molar ratio of sulfur to cobalt, calculated by assuming all molybdenum is present as $MoS_2$; and
(b) activating the precursor catalyst composition by contact with a stream comprising syngas, under suitable conditions for catalyst activation, thereby producing a second catalyst composition having a second molar ratio of sulfur to cobalt,
wherein the second molar ratio of sulfur to cobalt is lower than the first molar ratio of sulfur to cobalt.

In some embodiments, the first molar ratio of sulfur to cobalt is at least 1.2. In some embodiments, the second molar ratio of sulfur to cobalt is 1.5 or less.

The compositions can include a first amount of total cobalt contained in the precursor catalyst composition, which first total cobalt amount is capable of leaching into a 3N HCl solution, and a second amount of total cobalt contained in the activated catalyst composition, which second total cobalt amount is capable of leaching into a 3N HCl solution. The second amount of cobalt is greater than the first amount of cobalt, in some embodiments.

A fifth aspect of this invention provides methods of producing at least one $C_1$-$C_4$ alcohol from syngas, the method comprising:

(a) providing a reactor including a catalyst composition comprising cobalt, molybdenum, and sulfur, wherein at least some of the cobalt and some of the sulfur are present as a cobalt-sulfur association having a molar ratio of sulfur to cobalt (S:Co), calculated by assuming all molybdenum is present as $MoS_2$;

(b) flowing syngas into the reactor at conditions effective to produce at least one $C_1$-$C_4$ alcohol; and (c) injecting additional sulfur, or a compound containing sulfur, into the reactor in an amount that is sufficient to maintain at least some of the cobalt in a sulfided state, and is further sufficient to maintain the molybdenum in a completely sulfided state.

In some embodiments, the molar ratio S:Co is controlled to between about 0.1 and about 4, such as to a ratio of at least 1.

The additional sulfur injected in step (c) of this fifth aspect can be contained in one or more compounds selected from the group consisting of elemental sulfur, hydrogen sulfide, dimethyl disulfide, methylthiol, ethylthiol, cysteine, cystine, methionine, potassium disulfide, cesium disulfide, and sodium disulfide.

DETAILED DESCRIPTION OF EMBODIMENTS OF THE INVENTION

This description will enable one skilled in the art to make and use the invention, and it describes several embodiments, adaptations, variations, alternatives, and uses of the invention, including what is presently believed to be the best mode of carrying out the invention. As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

The present invention will now be described by reference to the following detailed description, which characterizes some preferred embodiments but is by no means limiting.

For present purposes, "catalyst composition" means a composition of a catalytic material that is not activated. An "activated catalyst composition" is a composition of a catalytic material that is suitably activated (or regenerated). By "activated" it is meant that the catalyst is exposed to conditions (such as, but not necessarily, reactor conditions) that render it more suitable for its intended purpose, which in this case means the conversion of syngas to alcohols.

Base promoters can enhance the production of alcohols from syngas. By "base promoter" it is meant one or more metals that promote the production of alcohols. Base promoters may be present in free or combined form. The base promoter can be present as a metal, oxide, carbonate, hydroxide, sulfide, as a salt, in a compound with another component, or some combination of the above.

It has been discovered that preferred variants of catalyst compositions for converting syngas to alcohols (e.g., $C_1$-$C_4$ alcohols) comprise cobalt-molybdenum-sulfide powders which have certain characteristic chemical signatures. These preferred catalyst compositions are relatively rich in sulfur. Specifically, the amount of sulfur present in preferred catalysts is higher than would be expected by a skilled artisan, based on typical oxidation numbers of cobalt and molybdenum in sulfide compounds.

In some embodiments, the amount of sulfur present is in excess of that expected if cobalt occurs as $CoS_2$ and molybdenum occurs as $MoS_2$. In some preferred embodiments, the amount of sulfur is in excess of that expected if cobalt occurs as $Co_3S_4$ and molybdenum occurs as $MoS_2$, as will be described in more detail below and in Examples 1 and 2.

Additionally, preferred compositions of cobalt-molybdenum-sulfide alcohol-synthesis catalysts are relatively unreactive toward gentle leaching into non-oxidizing aqueous mineral acids, such as hydrochloric acid. Furthermore, preferred variants of cobalt-molybdenum-sulfide catalysts are slightly more reactive toward sulfur leaching into solvents such as chloroform, as compared to less-preferred catalyst compositions.

As used herein, chloroform leaching of elemental sulfur refers to an analytical extraction of the sulfur into substantially pure chloroform ($CHCl_3$), conducted at a temperature selected from about 20° C. to about 55° C. or higher, and preferably at about 55° C. As is known, a variety of solvents are capable of extracting elemental sulfur into solution. It is preferable, but not critical, that chloroform is used. Other solvents that can be effective include toluene, methylene chloride, xylenes, benzene, acetone, carbon tetrachloride, and carbon disulfide. Some compositions of the present invention will be described in terms of chloroform leaching, and it will be appreciated that similar results can be obtained by leaching into other solvents effective for elemental sulfur.

As used herein, hydrochloric acid leaching of a metal refers to an analytical extraction of the metal into a solution of 3N HCl, conducted at room temperature (such as about 25° C.) or at higher temperature (such as about 90° C.). Other acids can be effective. Generally, a moderately strong, non-oxidizing mineral acid is preferred. For example, dilute solutions of one or more acids selected from HBr, HI, $HBF_4$, or $HPF_6$ can be used. Preferably, acid concentrations for the leaching tests are low enough to avoid possible total digestion of the material. In HCl, which is preferred, an additional role of chloride is thought to stabilize oxospecies of molybdenum in the leachate with respect to reprecipitation. It is noted that a metal may be leached in non-elemental forms, such as aqueous cations or aqueous salts.

In some embodiments of Co—Mo—S catalyst compositions provided by the present invention, sulfur is present in a total (free or combined form) amount of at least 40 wt % of the catalyst composition. In some preferred embodiments, total sulfur is between 42-44 wt % of the composition.

Preferred compositions do not contain very much elemental sulfur (typically regarded as $S_8$); i.e., they are not a mere physical mixture of sulfur with the other elements present. A non-zero amount of elemental sulfur can be present in preferred compositions. Namely, favored sulfided catalysts include elemental sulfur in an amount of at least about 100 ppm, calculated on a total-catalyst weight basis. The concentration of elemental sulfur is preferably between about 150-5000 ppm, more preferably between about 300-1000 ppm. Amounts higher than 5000 ppm of elemental sulfur can be effective from a catalysis standpoint, but there are practical concerns. For example, high levels of elemental sulfur in the compositions can melt and/or sublime in the catalyst bed, leading to operational problems. High levels of elemental sulfur could also lead to undesired formation of hydrogen sulfide or carbonyl sulfide.

The amount of elemental sulfur present in preferred catalysts can also be related to convenient chloroform leaching tests as described above. In certain embodiments, at least about 0.02% (but preferably not more than about 0.1%) of the total sulfur present is capable of leaching into chloroform. It is preferable that at least about 0.05% of the sulfur be capable of leaching into chloroform.

Preferred catalyst compositions for converting syngas into alcohols are highly sulfided, with cobalt associated with sulfide. In some embodiments, dispersed and crystalline $CoS_2$ is present in these catalysts. It is known that high-valency transition metals can oxidize sulfur to disulfide ($S_2^{2-}$) or even polysulfide species, with associated reduction at the metal center. Polysulfides are anions with the general formula $S_n^{2-}$ (n>2) and the general structure $^-SS_{n-2}S^-$.

The molar ratio of sulfur to cobalt ("S:Co"), given an initial assignment of sulfur to molybdenum to yield $MoS_2$, is regarded as an important parameter. As used herein, S:Co is calculated after assigning some of the sulfur to molybdenum by assuming all molybdenum is present in the catalyst composition as $MoS_2$. The S:Co molar ratio can optionally be calculated after subtracting sulfur that is capable of leaching into chloroform (or a similarly effective solvent), which will tend to account for elemental sulfur. The S:Co molar ratio can also optionally be calculated after subtracting sulfur that is capable of leaching into 3 N HCl (or a similarly effective dilute acid), which will tend to account for sulfur in the form of sulfates, sulfites, persulfates, hyposulfites, and the like. In some embodiments, the S:Co molar ratio can be calculated to account for all forms of sulfur that are soluble in (i.e., capable of leaching into) both chloroform and 3 N HCl. Preferred compositions do not have excessive amounts of these forms of sulfur, so the calculated S:Co molar ratios are typically not especially sensitive to the exclusion of sulfur species that are soluble in chloroform and/or 3 N HCl.

The S:Co molar ratio in the cobalt-sulfur association is at least about 1.2. Preferably, the molar ratio S:Co is at least about 1.5, and more preferably at least about 2.0. In some embodiments, S:Co is between about 2.0 and about 4.0. For example, for illustration purposes only, various specific embodiments of the invention can employ S:Co ratios of about 1.2, 1.3, 1.35 (i.e., slightly higher than what would be expected if cobalt were present as $Co_3S_4$), 1.4, 1.5, 1.75, 1.95, or 2.0. Various other specific embodiments can use S:Co ratios of about 2.05, 2.1, 2.2, 2.3, 2.4, 2.5, 2.6, 2.7, 2.8, 2.9, or 3.0. In other embodiments, S:Co ratios can exceed 3.0, such as up to and including about 4.0 or higher. These higher S:Co ratios can occur, for instance, when polysulfide anions are associated with cobalt.

In some embodiments of Co—Mo—S catalyst compositions, cobalt is present in an amount between about 3-21 wt %, preferably between about 10-16 wt %, and more preferably between about 13-15 wt % (wherein wt % is weight percent based on the total catalyst composition). In some embodiments of Co—Mo—S catalyst compositions, molybdenum is present in an amount between about 33-56 wt %, preferably between about 35-50 wt %, and more preferably between about 40-45 wt %.

In preferred embodiments, the molar ratio of molybdenum to cobalt, Mo:Co, can generally be between about 1 and about 20, preferably between about 1.5 and about 8, and more preferably about 2.

The mass fraction of total sulfur (i.e. sulfur in free or combined form) is preferably greater than 40 wt % for catalyst compositions when the Mo:Co mole ratio is about 2. Alcohol-synthesis catalysts can, however, use Mo:Co mole ratios different from 2, as described above. As the Mo:Co mole ratio varies, the desirable mass fraction of sulfur will also preferably vary. In preferred embodiments, the catalyst composition includes sufficient sulfur so that all Mo can occur as $MoS_2$, with additional sulfur so as to maintain cobalt in a sulfided state.

It is preferable that the catalyst composition includes sulfur in an oxidation state that is relatively high, for the sulfur in association with cobalt. In some embodiments, the average oxidation number for sulfur in association with cobalt is greater than −2, preferably at least about −1.5, and more preferably about −1. Average sulfur oxidation states can be in the range of −2 to −1 or higher, according to the present invention, for the sulfur in association with cobalt.

In $CO_3S_4$, wherein S:Co=1.33, the oxidation number of cobalt is both +2 and +3 (formally $CO_3S_4$ is [Co(II)][Co(III)]$_2S_4$). The average oxidation state of sulfur in $CO_3S_4$ is −2. In $CoS_2$, wherein S:Co=2, the oxidation number of cobalt is +2 and the sulfur oxidation number is −1. Cobalt-sulfur associations having higher S:Co molar ratios are expected to have higher (less negative) sulfur oxidation numbers. In light of the preferred S:Co molar ratios as described above, preferred embodiments of the catalyst compositions of the invention will include at least a portion of sulfur in the −1 oxidation state.

The amount and nature of cobalt present in preferred catalysts can be related to convenient hydrochloric acid leaching tests as described above. In some embodiments, less than about 8% of the total cobalt present is capable of leaching into a 3N HCl solution. It is preferable that less than about 5%, 3%, 2%, 1%, or less (including substantially none) of the total cobalt is capable of leaching into 3N HCl. "Substantially none" means that no metal is measured by standard detection techniques, but a small amount may in fact be present in the 3N HCl leachate.

The amount and nature of molybdenum present in preferred catalysts can be related as well to these convenient hydrochloric acid leaching tests. In some embodiments, less than about 1.0% of the total molybdenum present is capable of leaching into a 3N HCl solution. It is preferable that less than about 0.5%, 0.3%, 0.2%, 0.1%, or less (including substantially none) of the total molybdenum is capable of leaching into 3N HCl.

Other aspects of the invention relate to preferred sulfide stoichiometries pertaining to nickel-molybdenum-sulfide, cobalt-tungsten-sulfide, and nickel-tungsten-sulfide catalyst compositions. When Ni is employed rather than Co, the amount of sulfur present will be in excess of that which would be expected if Mo occurs as $MoS_2$ and Ni as NiS. When tungsten is used rather than molybdenum, the amount of sulfur present will be in excess of that which would occur if cobalt were present as CoS, or nickel as NiS, and tungsten present as $WS_2$.

Some embodiments of the present invention provide a catalyst composition for catalyzing the conversion of syngas into alcohols, the composition comprising sulfur, a first element or plurality of elements E1 and a second element or plurality of elements E2, wherein: E1 is cobalt and/or nickel; E2 is molybdenum and/or tungsten; at least some of E1 and some of the sulfur are present as an E1-sulfur association; and the molar ratio of sulfur to E1 (S:E1) in the association is at least 1.2, the molar ratio S:E1 calculated after assigning some of the sulfur to E2 by assuming all E2 is present in the composition as $E2S_2$, and optionally after subtracting any sulfur that is soluble in chloroform and/or 3 N HCl. In certain embodiments, the molar ratio S:E1 is at least 1.5, preferably between about 2.0 and about 4.0, selected in a similar manner as described above for S:Co.

E1 can be present in an amount between about 2 wt % and about 25 wt %, and E2 can be present in an amount between about 25 wt % and about 95 wt % of the composition. In some embodiments, E1 is present in an amount between about 10-25 wt % of the composition, and E2 is present in an amount between about 25-60 wt %.

In some embodiments, total sulfur is present in a total amount of at least 30 wt % of the composition. This total sulfur preferably includes at least 100 ppm elemental sulfur. In certain preferred embodiments, at least 0.02% of the sulfur is capable of leaching into chloroform at 25° C. In preferred embodiments, less than about 5% of E1 and less than about 0.5% of E2 is capable of leaching into a 3N HCl solution at 25° C.

Generally, preferred Ni—Mo—S, Co—W—S, or Ni—W—S catalysts will be similarly resistant toward leaching metals into gentle mineral acid, as are preferred Co—Mo—S catalysts. As will be appreciated by a skilled artisan, similar methods can be recited for catalysts containing complex mixtures, such as Co—Ni—Mo—W—S catalysts.

Aspects of the present invention also relate to methods of making these catalyst compositions. The catalytic species may be dispersed by methods known in the art. Examples include impregnation from solution followed by conversion to the sulfided species or intimate physical mixing. One or more of these methods may be used. It is preferred that at least two of the catalytic components (i) Mo and/or W, (ii) Co and/or Ni, and (iii) S are intimately mixed. More preferably, all of these catalyst components are substantially intimately mixed.

In some embodiments, the catalyst composition further includes at least one base promoter which can increase selectivities to alcohols from syngas. In some embodiments, at least one base promoter includes one or more elements selected from the group consisting of potassium, rubidium, cesium, barium, strontium, scandium, yttrium, lanthanum, or cerium, in free or combined form.

The base promoter is preferably at least present at a level sufficient to render the catalyst more basic. The base promoter is generally present in an amount of at least about 0.01 wt %, with metal promoters calculated as if a free element in the catalyst. Preferably, the base promoter is present in an amount of at least 0.1 wt %, more preferably between about 1 wt % and 20 wt %.

The base promoter may be added as an ingredient to a catalytic component or to a support, or may be part of one of the catalytic components or as an integral part of the support. The base promoter may be added to the active catalytic element prior to, during, or after the formation of the sulfide. For example, physical mixing or solution impregnation may be employed.

In certain embodiments of the present invention, ammonium tetrathiomolybdate can by made by addition of ammonium sulfide solution or hydrogen sulfide gas to a solution of a soluble molybdate, such as (for example) ammonium heptamolybdate. To this solution, cobalt acetate solution may be added to provide a suspension wherein the Mo:Co ratio is about 2. Without being limited by any particular theory, it is presently believed that these embodiments take advantage of the insolubility of the $[NH_4^+]_2[Mo_2CoS_8^{2-}]$ salt.

If Mo:Co mole ratios different from two are desired, some $[NH_4^+]_2[Mo_2CoS_8^{2-}]$ salt still forms. When cobalt is in excess, it may coprecipitate by assuring an excess of sulfide anion is present at the time of cobalt precipitation, resulting in an intimately mixed precipitate. This precipitate comprises an amorphous cobalt sulfide and $[NH_4^+]_2[Mo_2CoS_8^{2-}]$ salt. If Mo is desired to be present in excess of Mo:Co=2:1, its precipitation may be favored by controlling the temperature of coprecipitation at a temperature lower than about 50° C. Solubility of ammonium tetrathiomolybdate is rather strongly temperature dependent, decreasing at lower temperatures. Nickel and tungsten react with very similar trends.

To the $[NH_4^+]_2[Mo_2CoS_8^{2-}]$ precipitate, an aqueous solution of, for example, an acetate salt of a lanthanide-series metal or of barium or strontium may be added by incipient-wetness impregnation. The composition is then calcined under inert conditions, in certain embodiments. "Inert conditions" with respect to calcining means that (i) the atmosphere at the inlet to the calciner (or other apparatus effective for calcining Co—Mo—S materials) is substantially free of $O_2$ and $H_2O$, and further that (ii) separation of $H_2O$ and volatile components (such as $NH_3$, $S_8$, and the like) from the solid catalyst phase is efficient. $N_2$ and Ar, if suitably free of contaminating water and oxygen, represent suitable carrier gases for the calcinations.

Alternately, the ammonium cobalt thiomolybdate may be calcined under inert conditions prior to addition of the base promoter. In this case, it is typically convenient to grind, under a substantially inert atmosphere, a salt (e.g., an acetate or carbonate salt) of a base promoter such as potassium or cesium.

The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In embodiments of the invention that employ a catalyst support, the support is preferably (but not necessarily) a carbon-rich material with large mesopore volume, and further is preferably highly attrition-resistant. One carbon support that can be utilized is "Sibunit" activated carbon (Boreskov Inst. of Catalysis, Novosibirsk, Russia) which has high surface area as well as chemical inertness both in acidic and basic media (Simakova et al., Proceedings of SPIE—Volume 5924, 592413, 2005). An example of Sibunit carbon as a catalyst support can be found in U.S. Pat. No. 6,617,464 (Manzer).

The present invention also relates to use of catalyst compositions. In some embodiments of the invention, a reactor is loaded with a catalyst comprising a composition as described herein. A process stream comprising syngas is fed into the reactor at conditions effective for producing alcohols from the syngas.

In some embodiments, conditions effective for producing alcohols from syngas include a feed hydrogen/carbon monoxide molar ratio ($H_2/CO$) from about 0.2-4.0, preferably about 0.5-2.0, and more preferably about 0.5-1.5. These ratios are indicative of certain embodiments and are not limiting. It is possible to operate at feed $H_2/CO$ ratios less than 0.2 as well as greater than 4, including 5, 10, or even higher. It is well-known that high $H_2/CO$ ratios can be obtained with extensive steam reforming and/or water-gas shift in operations prior to the syngas-to-alcohol reactor.

In embodiments wherein $H_2/CO$ ratios close to 1:1 are desired for alcohol synthesis, partial oxidation of the carbonaceous feedstock can be utilized. In the absence of other reactions, partial oxidation tends to produce $H_2/CO$ ratios close to unity, depending on the stoichiometry of the feedstock.

When, as in certain embodiments, relatively low $H_2/CO$ ratios are desired, the reverse water-gas shift reaction ($H_2 + CO_2 \rightarrow H_2O + CO$) can potentially be utilized to consume hydrogen and thus lower $H_2/CO$. In some embodiments, $CO_2$ produced during alcohol synthesis or elsewhere, can be recycled to the reformer to decrease the $H_2/CO$ ratio entering the alcohol-synthesis reactor. Other chemistry and separation approaches can be taken to adjust the $H_2/CO$ ratios prior to converting syngas to alcohols, as will be appreciated. For example, certain commercial membrane systems are known to be capable of selectively separating $H_2$ from syngas, thereby lowering the $H_2/CO$ ratio.

In some embodiments, conditions effective for producing alcohols from syngas include reactor temperatures from about 200-400° C., preferably about 250-350° C.; and reactor pressures from about 20-500 atm, preferably about 50-200 atm or higher. Generally, productivity increases with increasing reactor pressure. Temperatures and pressures outside of these ranges can be employed.

In some embodiments, conditions effective for producing alcohols from syngas include average reactor residence times from about 0.1-10 seconds, preferably about 0.5-2 seconds. "Average reactor residence time" is the mean of the residence-time distribution of the reactor contents under actual operating conditions. Catalyst space times or catalyst contact times can also be calculated by a skilled artisan and these times will typically also be in the range of 0.1-10 seconds, although it will be appreciated that it is certainly possible to operate at shorter or longer times.

In general, the specific selection of catalyst configuration (geometry), $H_2/CO$ ratio, temperature, pressure, residence time (or feed rate), and other reactor-engineering parameters will be selected to provide an economical process. These parameters are not regarded as critical to the present invention. It is within the ordinary skill in the art to experiment with different reactor conditions to optimize selectivity to a particular product or some other parameter.

Product selectivities can be calculated on a carbon-atom basis. "Carbon-atom selectivity" means the ratio of the moles of a specific product to the total moles of all products, scaled by the number of carbon atoms in the species. This definition accounts for the mole-number change due to reaction. The selectivity $S_j$ to general product species $C_{xj}H_{yj}O_{zj}$ is $$S_j = \frac{x_j F_j}{\sum_i x_i F_i}$$

wherein $F_j$ is the molar flow rate of species j which contains $x_j$ carbon atoms. The summation is over all carbon-containing species ($C_{xi}H_{yi}O_{zi}$) produced in the reaction.

In some embodiments, wherein all products are identified and measured, the individual product selectivities sum to unity (plus or minus analytical error). In other embodiments, wherein one or more products are not identified in the exit stream, the selectivities can be calculated based on what products are in fact identified, or instead based on the conversion of reactants. In the latter case, the selectivities may not sum to unity if there is some mass imbalance. Nevertheless, this method can be preferable as it tends to determine more accurate selectivities to identified products when it is suspected that at least one reaction product is not measured.

"$CO_2$-free carbon-atom selectivity" or "$CO_2$-free selectivity" mean the percent of carbon in a specific product with respect to the total carbon converted from carbon monoxide to some product other than carbon dioxide. It is the same equation above for $S_j$, except that $i \neq CO_2$ and $j \neq CO_2$.

In various embodiments of the present invention, the product stream from the reactor may be characterized by $CO_2$-free selectivities of about 10-40% to methanol and about 20-60% or higher to ethanol. In some preferred embodiments, the ethanol $CO_2$-free selectivity is higher, preferably substantially higher, than the methanol $CO_2$-free selectivity, such as a $CO_2$-free selectivity ratio of ethanol/methanol in the product of about 1.0, 1.5, 2.0, 2.5, 3.0, or higher. The product stream can also contain more methanol than ethanol, on either a mole basis or a carbon-atom basis, in certain embodiments. The $CO_2$-free selectivity ratio of ethanol to all other alcohols is preferably at least 1, more preferably at least 2.

The product stream from the reactor may include up to about 25% $CO_2$-free selectivity to $C_{3+}$ alcohols, and up to about 10% to other non-alcohol oxygenates such as aldehydes, esters, carboxylic acids, and ketones. These other oxygenates can include, for example, acetone, 2-butanone, methyl acetate, ethyl acetate, methyl formate, ethyl formate, acetic acid, propanoic acid, and butyric acid.

Another aspect of the invention relates to methods for activating, or otherwise generating, preferred activated catalyst compositions. In some embodiments, an activated catalyst composition is prepared by first providing a starting catalyst composition comprising cobalt, molybdenum, and sulfur, wherein at least some of the cobalt and some of the sulfur are present as a cobalt-sulfur association, and wherein the molar ratio of sulfur to cobalt (S:Co) in the association is at least 1.2, the molar ratio S:Co calculated by assuming all molybdenum is present in the catalyst composition as $MoS_2$. This starting catalyst composition is then subjected to a stream of syngas under suitable activation conditions, preferably in situ within the reactor, such that the S:Co molar ratio (calculated in the same way as for the starting catalyst composition) decreases to a ratio that is at least somewhat lower than the S:Co molar ratio in the starting catalyst composition. In various embodiments, the S:Co molar ratio decreases to about 1.5, 1.4, 1.3, 1.2, 1.1, 1.0, 0.9, 0.8, 0.7, 0.6, 0.5, 0.4, 0.3, 0.2, 0.1, or even less, provided at least some of the cobalt remains in a sulfided state.

In certain embodiments of this aspect relating to catalyst activation, with reference to the above-described hydrochloric acid leaching tests, a first amount of total cobalt contained in the starting catalyst composition is capable of leaching into a 3N HCl solution, and a second amount of total cobalt contained in the activated catalyst composition is capable of leaching into a 3N HCl solution. Preferably, the second amount of cobalt is greater than the first amount of cobalt that can leach. For example, when less than about 5% of the total cobalt present in the starting catalyst composition can leach into a 3N HCl solution, more than about 5% of the total cobalt present in the activated catalyst composition can leach into a 3N HCl solution. When less than about 1% of the total cobalt in the non-activated catalyst composition can leach into a 3N HCl solution, more than about 1% of the total cobalt in the activated catalyst composition can leach into such a solution.

During activation, the catalyst can become more reduced, with evolution of various light sulfur compounds such as $H_2S$, $CH_3SH$, $CH_3SCH_3$, $CH_3CH_2SH$, and the like. In some variations, it can be beneficial (but is by no means necessary) to add sulfide back to the activated or operating catalyst composition to compensate for the sulfur that evolves during activation or operation. Yet another aspect of the present invention provides methods to maintain certain sulfide levels in the activated catalyst compositions. In these methods, sulfur or a compound containing sulfur can be injected into the reactor, in an amount that is sufficient to maintain both the cobalt and the molybdenum in sulfided states.

In some embodiments of this aspect, additional sulfur is injected so as to control the molar ratio S:Co to between about 1.2 to about 2 or higher, up to about 4. Catalyst samples can be analyzed to measure S:Co and, if needed, additional sulfur can be introduced. Alternately, experiments can be separately conducted to establish that additional sulfur is necessary at certain times, or as a continuous injection in prescribed amounts, or some other program, in order to control (maintain) the S:Co ratio. S:Co is "measured and controlled" within the meaning herein whether the measurements are made prior to, or during, reactor operation.

In some embodiments, additional sulfur can be introduced by injecting, in dissolved form or another effective form, one or more compounds selected from the group consisting of elemental sulfur, hydrogen sulfide, dimethyl disulfide, methylthiol, ethylthiol, L-cysteine, D-cysteine, D,L-cysteine mixtures, L-cystine, D-cystine, D,L-cystine mixtures, L-methionine, D-methionine, D,L-methionine mixtures, potassium disulfide, cesium disulfide, and sodium disulfide. For the purpose of adding to the reactor, one or more of these compounds can be dissolved in, for example, toluene or other organic solvents. For the disulfides of potassium, sodium, or cesium, effective solvents can be selected from alcohols, short-chain polyethylene glycols, acetonitrile, DMF, DMSO, or THF.

Here, "injecting" sulfur can mean feeding sulfur into the reactor at the entrance, or introducing sulfur into the catalyst bed in any other way. Injecting includes introduction of sulfur as part of a syngas feed stream that comprises sulfur. Injecting can also include shutting down the normal operation of the reactor (syngas to alcohols) and then flowing a sulfur-containing compound through the catalyst bed in some fashion, to cause a change in the S:Co ratio.

EXAMPLES

Example 1

Performance of Compositions RF-1 and RF-2

Two catalyst compositions are produced and given the designations RF-1 and RF-2. Both compositions generally comprise Co—Mo—S and are produced in a similar manner, according to the description herein above, but the ultimate compositions that are obtained are different. The synthesis of RF-2 employs conditions that tend to exclude the atmosphere to a greater extent than the conditions for synthesis of RF-1.

In separate experiments, RF-1 and RF-2 catalysts are loaded into a reactor and tested for their capability to convert syngas into liquid products including ethanol. In these experiments, the primary variables are catalyst type (RF-1 or RF-2) and reactor temperature (310° C., 325° C., or 345° C.). A full-factorial experimental design is carried out, with 2×3=6 experiments. These experiments are each controlled to 30% CO conversion by adjusting space velocities.

Figure 1:
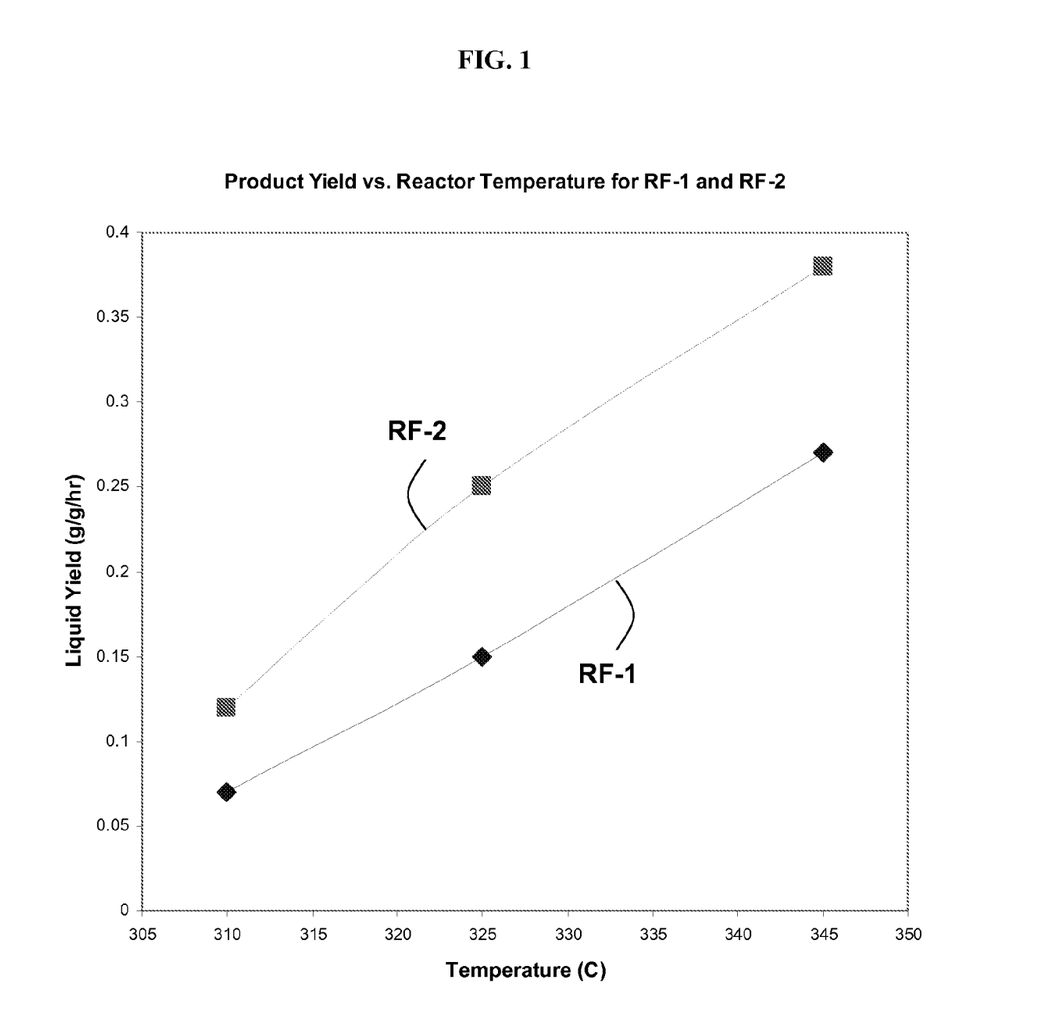
FIG. 1 is a graph depicting the effect of catalyst type and reactor temperature on experimental total-liquids yield.
Figure 2:
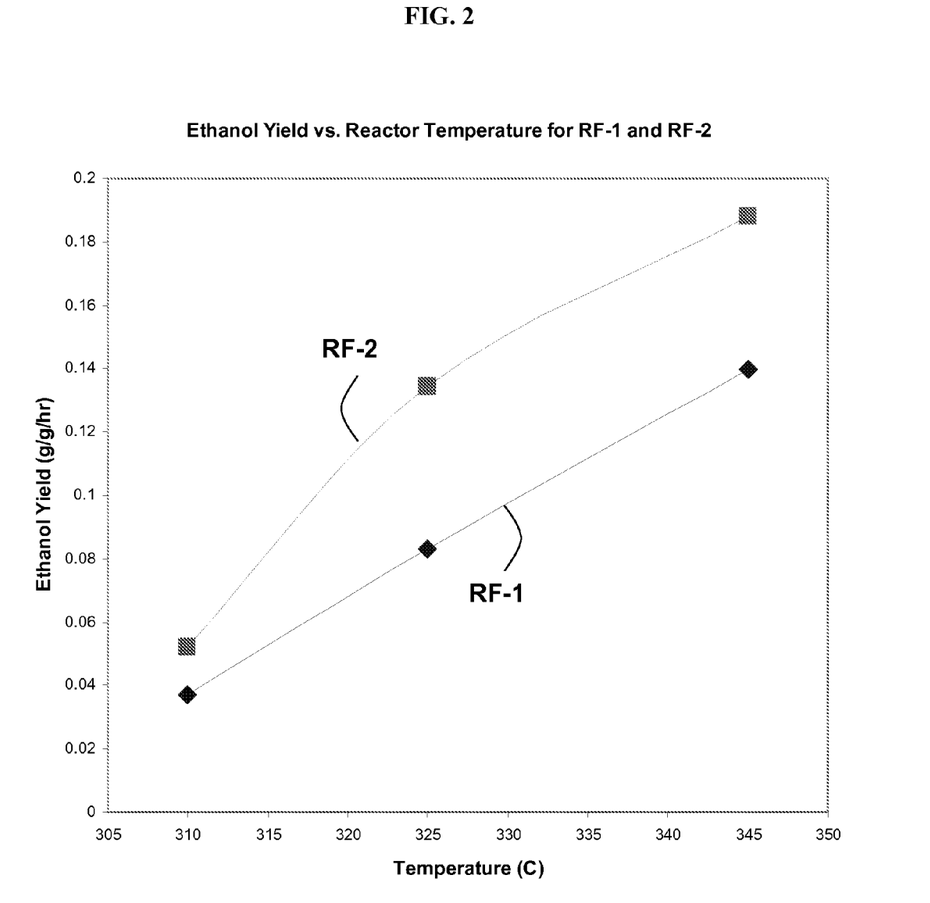
FIG. 2 is a graph depicting the effect of catalyst type and reactor temperature on experimental ethanol yield.

FIG. 1 shows the impact of catalyst and temperature on total liquid yield. FIG. 2 depicts the ethanol yield versus temperature, calculated as grams of liquid product per gram of catalyst per hour, for the two different catalysts RF-1 and RF-2. Also analyzed (not shown) are other alcohols including methanol, propanol, and butanol; water; and organic acids. From FIG. 2, it is experimentally observed that RF-2 is the superior catalyst of the two at any of the temperatures tested.

Example 2

Characterization of Compositions RF-1 and RF-2

The two catalyst compositions tested in actual reactors in Example 1, referred to as RF-1 and RF-2, are characterized in this example. The analysis for both compositions includes LECO S analysis, to determine total sulfur content; leaching the materials with chloroform, to assess the amount of elemental sulfur present; and leaching with 3N HCl, to assess the amount of hydrophilic, soluble sulfur, cobalt, and molybdenum. Three separate samples for each composition RF-1 and RF-2 are analyzed.

The mass fractions of total cobalt and total molybdenum are essentially the same for both RF-1 and RF-2, while the mass fractions of total sulfur are different (see tables below). The wt % numbers indicate the mean±standard deviation of the measurements. A t test value greater than 0.05 implies that there is no statistical basis to assert that differences exist, for that particular parameter, between RF-1 and RF-2.

|        | Total Co (wt %) | Total Mo (wt %) |
|--------|-----------------|-----------------|
| RF-1   | 14.43 ± 0.84    | 44.8 ± 2.2      |
| RF-2   | 13.67 ± 0.48    | 42.0 ± 2.4      |
| t test | 0.09            | 0.07            |

|        | Total S (wt %)      |
|--------|---------------------|
| RF-1   | 38.70 ± 0.80        |
| RF-2   | 42.71 ± 0.44        |
| t test | $6.1 \times 10^{-6}$ |

The amount of elemental sulfur (chloroform-leachable sulfur) is higher in RF-2 than in RF-1, as shown below. RF-2 is slightly more reactive toward leaching of elemental sulfur than RF-1. This result is consistent with a more highly sulfided, less hydrophilic or oxophilic material for catalyst composition RF-2.

| | Elemental Sulfur (wt %) |
|---|---|
| RF-1 | 0.0088 ± 0.0031 |
| RF-2 | 0.0382 ± 0.0045 |
| t test | 4.3 × 10⁻⁷ |

More cobalt and molybdenum from RF-1 leach into 3N HCl solution than from RF-2. The amounts of sulfur that leach into 3N HCl are comparable for the two materials.

Leachable Material into 3 Normal HCl Aqueous Solutions

| | wt % Leachable S | wt % Leachable Co | wt % Leachable Mo |
|---|---|---|---|
| RF-1 | 0.365 ± 0.074 | 1.49 ± 0.18 | 1.08 ± 0.17 |
| RF-2 | 0.432 ± 0.023 | 0.402 ± 0.042 | 0.125 ± 0.15 |
| t test | 0.08 | 1.1 × 10⁻⁵ | 3.2 × 10⁻⁵ |

RF-2 is relatively non-reactive toward metal leaching by 3N HCl. Given the assumption that Mo is present as $MoS_2$, as described above, a molar S:Co ratio can be calculated and the degree of sulfidation can be assessed.

| | S:Co Mole Ratio |
|---|---|
| RF-1 | 1.13 ± 0.27 |
| RF-2 | 1.97 ± 0.25 |
| t test | 2.3 × 10⁻⁴ |

Given the results of Example 1 (e.g., FIG. 2) in conjunction with the characterizations in Example 2, preferential aspects of compositions for higher-alcohol synthesis catalysts are revealed.

Example 3

Experimental Co:S Molar Ratios for Certain Preferred Catalyst Compositions of the Invention In this example, 18 distinct Co—Mo—S catalysts are synthesized in a manner experimentally similar to the procedure to synthesize RF-2 in Example 1. Due to imperfect process control, some variations in composition arise. A representative reactor experiment at 325° C. and 30% CO conversion (for reasons explained in Example 1) gives a liquid yield of about 0.21 g/g/hr and an ethanol yield of about 0.1 g ethanol per g catalyst per hour. With reference to the performance of RF-1 and RF-2, as shown in FIGS. 1 and 2, the performance of this single catalyst was measurably better than RF-1.

All 18 lots of catalyst in this example are analyzed by the same techniques as described in Example 2. It is of interest to consider the S:Co molar ratio, given an initial assignment of sulfur to molybdenum to yield $MoS_2$.

Figure 3:
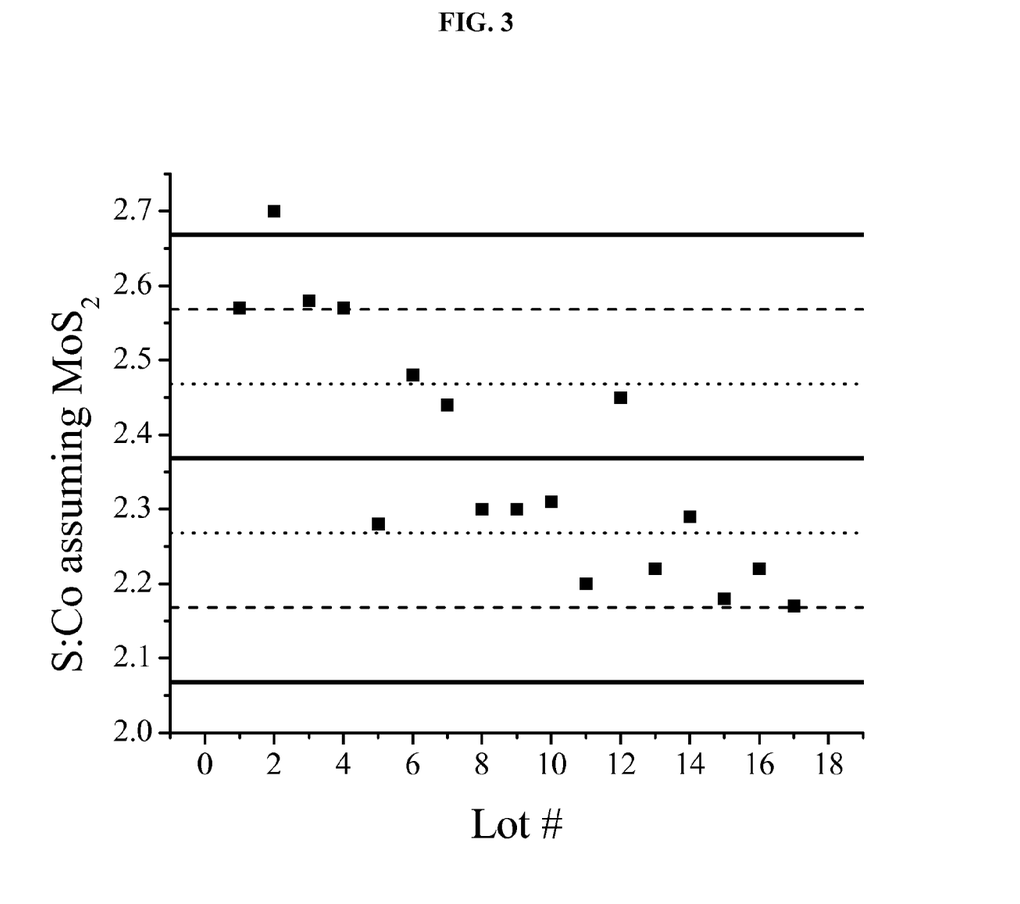
FIG. 3 is a chart showing S:Co molar ratios associated with certain preferred catalyst compositions.

FIG. 3 depicts the S:Co molar ratios across the 18 lots of catalysts synthesized in this example, wherein S:Co is calculated after subtracting elemental sulfur as determined by leaching into chloroform at room temperature. This ratio varies between about 2.2 and about 2.7, with an average of about 2.4.

Figure 4:
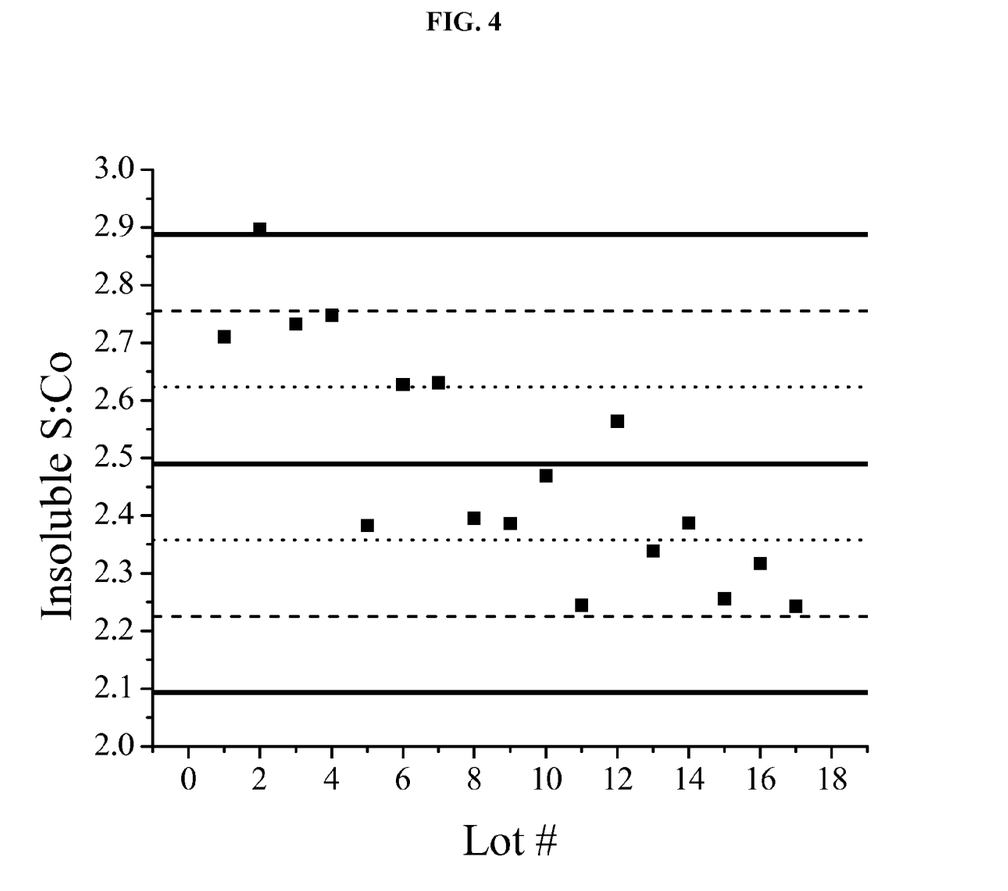
FIG. 4 is a chart showing S:Co molar ratios associated with certain preferred catalyst compositions.

FIG. 4 shows the S:Co molar ratios across the 18 lots of catalysts, wherein S:Co here subtracts the sulfur species (presumably primarily sulfate) soluble in 3 N HCl, as well as the sulfur that is soluble in chloroform. This ratio varies between about 2.2 and about 2.9, with an average of about 2.5. The lowest S:Co ratio observed here, 2.2, exceeds what would be expected if the sulfided components are present only as $MoS_2$ and $CoS_2$. Furthermore, the sulfur-to-cobalt ratio is significantly higher than what would be expected if cobalt is present as CoS and/or $CO_3S_4$.

Example 4

Evolution of Co:S Molar Ratios During Alcohol Synthesis

In this example, a Co—Mo—S powder with Mo:Co=2 (mole basis) and S:Co=2.1 (assuming Mo is present as $MoS_2$) is provided. This powder is compounded with $K_2CO_3$ such that Co:K=1 (mole basis), mixed with a binder, and formed into catalyst pellets. These pellets are loaded into reactors and operated under alcohol-synthesis conditions for varying periods of time as follows: sample A at 90 hours; sample B at 200 hours; and sample C at 500 hours. The pellets are then discharged under inert conditions and subjected to chemical analysis. Note that the three different samples herein are run in different reactors.

Catalyst sample A has a S:Co ratio of about 1.4 (assuming that Mo occurs as $MoS_2$), and 40-46% of the cobalt leaches into 3N HCl solution. Sample B has a S:Co ratio of about 0.5, and 50% of the cobalt leaches into 3N HCl solution. Sample C has a S:Co ratio of about 0.9, and 39-42% of the cobalt is extracted into 3N HCl.

It is therefore observed that a substantial fraction (about 40-50%) of cobalt is extracted into 3 HCl and the S:Co ratio varies from about 0.45 to 1.4 even though, initially, S:Co was about 2.1 and only a small portion (in the range of 0.5-7%) of cobalt leaches from the initial catalyst. By contrast, 10% of the Co in RF-1 catalyst (Example 1) extracts into 3N HCl and the S:Co ratio in RF-1 catalyst is about 1.1. A large fraction (35-55%) of Co in catalytically used RF-2 catalyst is extractable into 3N HCl, while only 10% of Co in RF-1 is extractable into 3N HCl.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the appended claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of producing at least one $C_1$-$C_4$ alcohol from syngas, the method comprising:
   (a) providing a reactor;
   (b) providing a first catalyst composition comprising cobalt, molybdenum, sulfur, and a base promoter, wherein at least some of said cobalt and some of said sulfur are present as a cobalt-sulfur association having a first molar ratio of sulfur to cobalt, calculated by assuming all molybdenum is present as $MoS_2$;
   (c) activating said first catalyst composition by contact with a stream comprising syngas, under suitable conditions for catalyst activation, thereby producing a second catalyst composition having a second molar ratio of sulfur to cobalt; and
   (d) flowing syngas into said reactor at conditions effective to produce at least one $C_1$-$C_4$ alcohol,
   wherein said second molar ratio of sulfur to cobalt is lower than said first molar ratio of sulfur to cobalt.

2. The method of claim 1, wherein said first molar ratio of sulfur to cobalt is at least 1.2.

3. The method of claim 1, wherein said second molar ratio of sulfur to cobalt is 1.5 or less.

4. The method of claim 3, wherein said second molar ratio of sulfur to cobalt is 0.5 or less.

5. The method of claim 1, wherein said first molar ratio of sulfur to cobalt is at least 2 and said second molar ratio of sulfur to cobalt is 1.4 or less.

6. The method of claim 1, wherein said activating step (c) is performed within said reactor provided in step (a).

7. The method of claim 1, wherein a first amount of total cobalt contained in said first catalyst composition is capable of leaching into a 3N HCl solution, a second amount of total cobalt contained in said second catalyst composition is capable of leaching into a 3N HCl solution, and said second amount of cobalt is greater than said first amount of cobalt.

8. The method of claim 7, wherein said first amount of total cobalt capable of leaching into a 3N HCl solution is less than about 10%.

9. The method of claim 7, wherein said second amount of total cobalt capable of leaching into a 3N HCl solution is greater than about 40%.

10. The method of claim 7, wherein said first amount of total cobalt capable of leaching into a 3N HCl solution is less than about 10% and wherein said second amount of total cobalt capable of leaching into a 3N HCl solution is greater than about 40%.

11. A method of producing at least one $C_1$-$C_4$ alcohol from syngas, the method comprising:
    (a) providing a reactor including a catalyst composition comprising cobalt, molybdenum, and sulfur, wherein at least some of said cobalt and some of said sulfur are present as a cobalt-sulfur association having a molar ratio of sulfur to cobalt (S:Co), calculated by assuming all molybdenum is present as $MoS_2$;
    (b) flowing syngas into said reactor at conditions effective to produce at least one $C_1$-$C_4$ alcohol; and
    (c) injecting additional sulfur, or a compound containing sulfur, into said reactor, in an amount that is sufficient to maintain at least some of said cobalt in a sulfided state, and is further sufficient to maintain said molybdenum in a completely sulfided state.

12. The method of claim 11, wherein said molar ratio S:Co is controlled to between about 0.1 and about 4.

13. The method of claim 12, wherein said molar ratio S:Co is controlled to a ratio of at least 1.

14. The method of claim 11, wherein said additional sulfur injected in step (c) is contained in one or more compounds selected from the group consisting of elemental sulfur, hydrogen sulfide, dimethyl disulfide, methylthiol, ethylthiol, cysteine, cystine, methionine, potassium disulfide, cesium disulfide, and sodium disulfide.

15. A composition for catalyzing the conversion of syngas into products comprising at least one $C_1$-$C_4$ alcohol, said composition comprising sulfur, a first element or plurality of elements E1, and a second element or plurality of elements E2, wherein:
    E1 is cobalt and/or nickel;
    E2 is molybdenum and/or tungsten;
    at least some of E1 and some of said sulfur are present as an E1-sulfur association; and
    the molar ratio of sulfur to E1 (S:E1) in said association is at least 1.2,
    said molar ratio S:E1 calculated after assigning some of said sulfur to E2 by assuming all E2 is present in said composition as $E2S_2$.

16. The composition of claim 15, wherein said molar ratio S:E1 is at least 1.5.

17. The composition of claim 15, wherein said sulfur is present in a total amount of at least 30 wt % of said composition.

18. The composition of claim 15, wherein said sulfur includes elemental sulfur in an amount of at least 100 ppm of said composition.

19. The composition of claim 15, wherein said molar ratio of said E2 to said E1 is from about 1.5 to about 8.

20. The composition of claim 15, further comprising one or more base promoters selected from the group consisting of potassium, rubidium, cesium, barium, strontium, scandium, yttrium, lanthanum, cerium, and any combinations thereof.

* * * * *